United States Patent
Yogesan et al.

(10) Patent No.: US 7,499,634 B2
(45) Date of Patent: Mar. 3, 2009

(54) OPHTHALMIC CAMERA, OPHTHALMIC CAMERA ADAPTOR AND METHODS FOR DETERMINING A HAEMOGLOBIN AND GLUCOSE LEVEL OF A PATIENT

(75) Inventors: Kanagasingam Yogesan, Nedlands (AU); Gabriel Suplewski, Iluka (AU); Matthew David Spark, High Wycombe (AU); Ian Constable, Nedlands (AU)

(73) Assignee: The Lions Eye Institute Ltd., Western Australia (AU)

( * ) Notice: Subject to any disclaimer, the term of this patent is extended or adjusted under 35 U.S.C. 154(b) by 401 days.

(21) Appl. No.: 11/311,057

(22) Filed: Dec. 19, 2005

(65) Prior Publication Data
US 2006/0147189 A1 Jul. 6, 2006

Related U.S. Application Data

(63) Continuation-in-part of application No. PCT/AU2004/000801, filed on Jun. 18, 2004.

(30) Foreign Application Priority Data
Jun. 20, 2003 (AU) ............................... 2003903157

(51) Int. Cl.
*A61B 3/14* (2006.01)
(52) U.S. Cl. ............................................ 396/18
(58) Field of Classification Search .................. 396/14, 396/16, 18; 348/78; 351/206
See application file for complete search history.

(56) References Cited

U.S. PATENT DOCUMENTS

| 2,478,545 | A | * | 8/1949 | Pearce ......................... 351/206 |
| 4,219,258 | A | * | 8/1980 | Araki et al. ................... 351/221 |
| 4,392,183 | A | * | 7/1983 | Ostlund et al. ................. 362/11 |
| 4,533,223 | A | * | 8/1985 | Duparchy ................... 351/206 |
| 4,586,796 | A | * | 5/1986 | Molteno ...................... 351/206 |
| 4,772,115 | A | * | 9/1988 | Gersten et al. ............... 351/212 |
| 5,285,223 | A |   | 2/1994 | Ueno et al. |

(Continued)

FOREIGN PATENT DOCUMENTS

CN 1101249 4/1995

(Continued)

OTHER PUBLICATIONS

International Search Report for International Application No. PCT/AU2004/000801, Sep. 21, 2004.

(Continued)

*Primary Examiner*—W. B. Perkey
(74) *Attorney, Agent, or Firm*—Frommer Lawrence & Haug LLP; Thomas J. Kowalski; Angela M. Collison

(57) ABSTRACT

Provided is an ophthalmic camera comprising: a camera having a camera lens; at least one illumination means; and an ophthalmic lens. The centres of the ophthalmic lens and camera lens are aligned to form an alignment axis. The at least one illumination means is capable of linear movement along a radial axis of the camera lens and pivotal movement about the radial plane incorporating radial axis and alignment axis. In such a manner, the circle of light emitted by the at least one illumination means is constantly directed to the centre of the ophthalmic lens.

64 Claims, 4 Drawing Sheets

U.S. PATENT DOCUMENTS

| | | | | |
|---|---|---|---|---|
| 5,294,948 | A | * | 3/1994 | Merkt et al. ................. 396/544 |
| 5,576,781 | A | * | 11/1996 | Deleeuw ....................... 396/6 |
| 6,305,804 | B1 | | 10/2001 | Rice et al. |
| 7,048,379 | B2 | * | 5/2006 | Miller et al. ................. 351/213 |
| 7,052,134 | B2 | * | 5/2006 | Nanjo et al. ................. 351/206 |
| 7,083,281 | B2 | * | 8/2006 | Yogesan et al. ............. 351/214 |
| 7,224,822 | B2 | * | 5/2007 | Heacock ..................... 382/117 |
| 2003/0011757 | A1 | | 1/2003 | Hirohara et al. |
| 2003/0050544 | A1 | | 3/2003 | Routt et al. |
| 2005/0200707 | A1 | * | 9/2005 | Yogesan et al. ........ 348/207.99 |
| 2005/0270484 | A1 | * | 12/2005 | Maeda et al. ............... 351/206 |
| 2008/0030679 | A1 | * | 2/2008 | Yogesan et al. ............. 351/206 |

FOREIGN PATENT DOCUMENTS

| | | |
|---|---|---|
| JP | 09266888 A | 4/1996 |
| JP | 10118030 A | 10/1996 |
| JP | 11299735 A | 4/1998 |
| JP | 2002051985 A | 8/2000 |
| WO | WO 97/37584 | 10/1997 |
| WO | WO 00/06017 | 2/2000 |
| WO | WO 03/012486 | 2/2003 |

OTHER PUBLICATIONS

Notification Of First Office Action Republic of China CN Application No. 200480017255.3, Aug. 31, 2007.

Supplementary European Search Report for EP Application No. 04737431, Jul. 30, 2007.

* cited by examiner

OPHTHALMIC CAMERA, OPHTHALMIC CAMERA ADAPTOR AND METHODS FOR DETERMINING A HAEMOGLOBIN AND GLUCOSE LEVEL OF A PATIENT

CROSS REFERENCE TO RELATED APPLICATIONS

This application is a continuation-in-part of International Application No. PCT/AU2004/000801, filed Jun. 18, 2004, published as WO 2004/112599 on Dec. 29, 2004, and claiming priority to Australian Application No. 2003903157, filed Jun. 20, 2003.

The foregoing applications, as well as all documents cited in the foregoing applications ("application documents") and all documents cited or referenced in the application documents are incorporated herein by reference. Also, all documents cited in this application ("herein-cited documents") and all documents cited or referenced in herein-cited documents are incorporated herein by reference. In addition, any manufacturer's instructions or catalogues for any products cited or mentioned in each of the application documents or herein-cited documents are incorporated by reference. Documents incorporated by reference into this text or any teachings therein can be used in the practice of this invention. Documents incorporated by reference into this text are not admitted to be prior art.

FIELD OF THE INVENTION

The present invention relates to an ophthalmic camera, ophthalmic camera adaptor and methods for determining a haemoglobin and glucose level of a patient. In particular, the invention relates to a miniaturised ophthalmic camera adaptor for non-mydriatic use.

BACKGROUND OF THE INVENTION

The following discussion of the background to the invention is intended to facilitate an understanding of the present invention. However, it should be appreciated that the discussion is not an acknowledgement or admission that any of the material referred to was published, known or part of the common general knowledge of a skilled person in any jurisdiction as at the priority date of the application.

The eye is a complex structure having multiple layers and sub-structures. In order to obtain a diagnosis of certain adverse conditions of the eye, images of one or more layers or sub-structures need to be captured.

Previously, such images were obtained by the use of a monochromatic camera having narrow wavelength coloured paper filters covering an associated light source. However, this arrangement produces deficiencies, namely:

- Light passing through a paper filter typically has a variable wavelength reflecting the variations in the surface of the paper filter;
- The associated light source is typically brighter than is needed to illuminate the eye; and
- As different layers of sub-structures of the eye need to be imaged, time needs to be spent in changing the paper filter.

It is therefore an object of the present invention to provide an optical arrangement that alleviates some or all of the problems associated with the prior art.

SUMMARY OF THE INVENTION

Throughout the specification, unless the context requires otherwise, the word "comprise" or variations such as "comprises" or "comprising", will be understood to imply the inclusion of a stated integer or group of integers but not the exclusion of any other integer or group of integers.

In accordance with a first embodiment of the invention there is an ophthalmic camera comprising:
  a camera having a camera lens;
  at least one illumination means; and
  an ophthalmic lens, where, the centres of the ophthalmic lens and camera lens are aligned to form an alignment axis and where the at least one illumination means is capable of linear movement along a radial axis of the camera lens and pivotal movement about the radial plane incorporating radial axis and alignment axis, such that the circle of light emitted by the at least one illumination means is constantly directed to the centre of the ophthalmic lens.

Preferably, the ophthalmic camera further comprises selection means for choosing from a plurality of settings, each setting representing a pupil size or range of pupil sizes, such that, when the setting is changed, the at least one illumination means moves linearly along its radial axis to the position specified by the new setting and pivots about the radial plane until the circle of light emitted by the at least one illumination means is directed on the centre of the ophthalmic lens.

Alternatively, the linear and pivotal movement of the at least one illumination means is controlled by one or more manual controls.

As yet a further alternative, the ophthalmic camera comprises automated measuring means for obtaining a measurement of the size of the pupil to be examined, the automated measuring means also controlling the linear and pivotal movement of the at least one illumination means to a position determined best for the measured pupil size.

Preferably, the ophthalmic camera comprises at least one magnification lens, each magnification lens being associated with at least one linear position of the at least one illumination means, such that the linear position of the at least one illumination means determines which magnification lens are positioned within the alignment axis.

Preferably, one of the at least one illumination means has a wavelength in the range 450 to 490 nm. Ideally, the illumination means has a wavelength of 490 nm.

Preferably, one of the at least one illumination means has a wavelength in the range 491 to 559 nm. Ideally, the illumination means has a wavelength of 540 nm.

Preferably, one of the at least one illumination means has a wavelength in the range 560 to 595 nm. Ideally, the illumination means has a wavelength of 590 nm.

Preferably, one of the at least one illumination means has a wavelength in the range 596 to 699 nm. Ideally, the illumination means has a wavelength of 630 nm.

Preferably, one of the at least one illumination means has a wavelength of 700 nm.

Preferably, one of the at least one illumination means produces white light.

Preferably, the camera is a digital camera or an analogue camera with digitising means for producing a digital representation of analogue images taken by the analogue camera.

Preferably, the at least one illumination means, or a subset of the at least one illumination means, is illuminated in accordance with a predetermined sequence.

Preferably, the ophthalmic camera has at least one interface means for connecting to at least one of the following: an external computer, an external monitor, an external spectrometer.

Preferably, the ophthalmic camera comprises a spectrometer, the spectrometer operable to produce a spectroscopic graph of images taken by the camera.

Preferably, the at least one illumination means is of variable intensity. Ideally, the level of intensity of the at least one illumination means is a function of a pupil colour setting of the ophthalmic camera.

Preferably, each of the at least one illumination means surrounds the circumference of the camera lens.

Preferably, each illumination means is equidistant from its adjacent illumination means.

Preferably, the illumination means are solid state light emitting diodes. Alternatively, the illumination means comprises light bulbs and a light focusing means.

Preferably, the camera has a high sensitivity to low light. Ideally, the sensitivity level of the camera is <0.05 lux.

Preferably, the camera lens is between 5 and 8 mm in diameter.

Preferably, the ophthalmic lens is in the range of 20 to 40 dioptres. Ideally, the ophthalmic lens is 20 dioptres.

Preferably, the ophthalmic camera further comprises focusing means. Ideally, the focusing means takes the form of movement means operable to move the ophthalmic lens linearly along the alignment axis.

Preferably, the ophthalmic lens is equal to or smaller than the camera lens.

In accordance with a second embodiment of the present invention there is an ophthalmic camera adaptor comprising:
at least one illumination means; and
an ophthalmic lens, where, the centres of the ophthalmic lens and camera lens are aligned to form an alignment axis and where the at least one illumination means is capable of linear movement along a radial axis of the camera lens and pivotal movement about the radial plane incorporating radial axis and alignment axis, such that the circle of light emitted by the at least one illumination means is constantly directed to the centre of the ophthalmic lens.

The ophthalmic camera adaptor has all of the additional features of the ophthalmic camera as appropriate.

In accordance with a third embodiment of the present invention, there is a wearable frame having at least one ophthalmic camera according to the first embodiment of the invention fixed thereon.

In accordance with a fourth embodiment of the present invention, there is a wearable frame having at least one ophthalmic camera according to the first embodiment of the invention slidably mounted thereon.

In accordance with a fifth embodiment of the present invention, there is a method of determining a glucose level of a patient, comprising:
emitting a beam of light having a wavelength in the range 570 to 590 nm into a pupil of the patient;
taking an image of the pupil using a camera having an associated ophthalmic lens of at least 20× magnification; and
determining the glucose level of the patient from information ascertainable from the image of blood in the veins of the optic disc.

In accordance with a sixth embodiment of the present invention, there is a method of determining a haemoglobin level of a patient, comprising:
emitting a beam of light having a wavelength in the range 570 to 590 nm into a pupil of the patient;
taking an image of the pupil using a camera having an associated ophthalmic lens of at least 20× magnification;
determining the haemoglobin level of the patient from the image of the macula.

BRIEF DESCRIPTION OF THE DRAWINGS

The invention will now be described, by way of example only, with reference to the accompanying drawings, of which.

DETAILED DESCRIPTION

Figure 1:
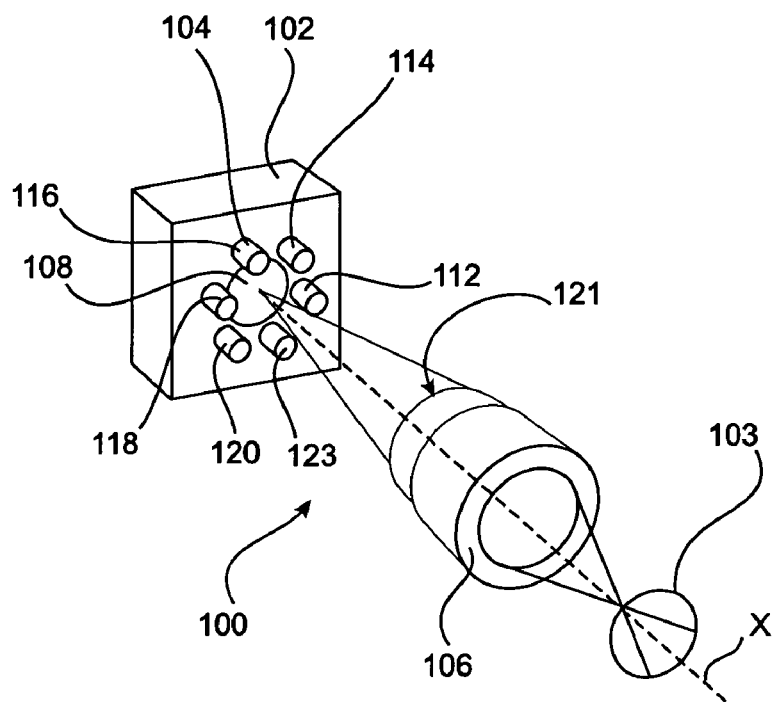
FIG. 1 is a schematic of the optics of an ophthalmic camera and ophthalmic camera adaptor of the present invention.
Figure 2:
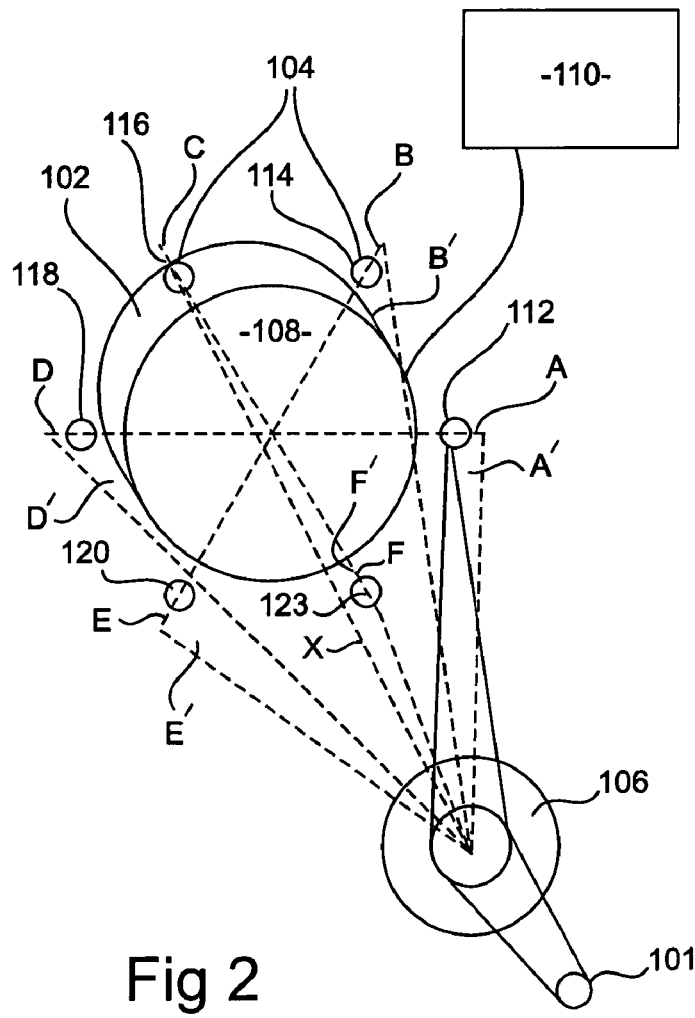
FIG. 2 is an isometric view of the optics of the ophthalmic camera and ophthalmic camera adaptor shown in FIG. 1.

In accordance with a first embodiment of the invention there is provided an ophthalmic camera 100 comprising a monochromatic camera 102 highly sensitive to low light (ie. somewhere in the range of <0.05 lux), a plurality of solid-state LEDs 104 and an ophthalmic lens 106 all contained within a housing (not shown).

The monochromatic camera 102 has a camera lens 108. Ideally, the camera lens 108 has a diameter of 5-8 mm. This is because lenses of a greater diameter have been found to produce circular occlusions on the resulting image.

The plurality of LEDs 104 surround the circumference of the camera lens 108 and are linked to a control unit 110. Each LED 104 is equidistant to its adjacent LEDs 104.

LEDs 104 are able to move linearly along their respective radial axes (marked A through E). Each LED 104 is able to pivot towards, or away from the camera lens 108 about the plane (marked A' through E') extending from its respective radial axis A-E.

The ophthalmic lens 106 has an inner surface 121 which opposes the camera lens 118. The centre of the camera lens 118 aligns with the centre of the inner surface 121. Ideally, the ophthalmic lens 106 is of the same size as, or smaller than, camera lens 108 and positioned within optical axis X of the monochromatic camera 102.

The ophthalmic lens 106 is typically in the range of 20 to 40 dioptres, with 20 dioptres considered optimal. To allow for focusing of the ophthalmic lens 106, the ophthalmic lens 106 is capable of linear movement along optical axis X of the monochromatic camera 102.

The position of the LEDs 104 is a function of the current setting of the ophthalmic camera 100. Each setting of the ophthalmic camera 100 represents a range of pupil 101 sizes. To elaborate,
setting 1 is used for pupils 101 of size less than 3 mm;
setting 2 is used for pupils 101 having a size between 3-4 mm; and
setting 3 is used for dilated pupils 101.

Upon choosing a setting LEDs 104 move, from their present linear and pivotal position, linearly along their respective radial axes (marked A through F) and pivot about their respective axial plane (marked A' through F') to the position represented by the newly chosen setting, such that, at this new position, the centre of the circle generated by the light emitted by the LED 104 at the point of intersection with the ophthalmic lens 116 is substantially equal to the centre of the inner surface 121 thereof.

In the embodiment shown:
LED 112 generates a homogenous blue light having a wavelength somewhere in the range 450 to 490 nm;
LED 114 generates a homogenous green light having a wavelength somewhere in the range of 491 to 559 nm;
LED 116 generates a homogenous yellow light having a wavelength somewhere in the range 560 to 595 nm;
LED 118 generates a homogenous red light having a wavelength somewhere in the range 596 to 699 nm; and
LED 120 generates a homogenous infrared light having a wavelength of 700 nm.
LED 123 generates a white light having a wavelength spanning the spectrum of 390 nm to 699 nm.

Ideally, LEDs 112, 114, 116, 118 and 120 have wavelengths of 490 nm, 540 nm, 590 nm, 630 nm and 700 nm, respectively.

The optical arrangement described above is shown in FIG. 1.

In use, the user manipulates the control unit 110 to illuminate one of the LEDs 104. The LED 104 that is illuminated is determined by the area of the eye to be imaged. In this regard:
if an image of the optic nerve fibres is desired, blue LED 112 is illuminated;
if an image of the cotton wool spots or veins is desired, green LED 114 is illuminated;
if an image useful for diabetic retinopathy or an image of the eye 103 of good overall contract is desired, yellow LED 116 is illuminated;
if an image of the surface of the choroids is desired, red LED 118 is illuminated. Depending on the wavelength of the red LED 118, the captured image may show some elements of the choroid below the surface;
if an image of elements below the surface of the choroid is desired, infrared LED 120 is illuminated; and
if a standard image of the eye is desired, white LED 123 is illuminated.

Once the desired LED 104 is illuminated, the ophthalmic lens 106 is moved along optical axis X until the image to be captured, as determined at the point of the monochromatic camera 102, is focused. The image can then be captured as per the mechanisms for doing so provided by the monochromatic camera 102 used.

Ideally, LED 116 has an wavelength in the range 570 to 590 nm. Taking an image using LED 116 with an ophthalmic lens 106 having 20× magnification, allows a clear, sizable, picture of the veins of the optic disc and the macula. Using this image, the glucose level of the patient can be determined from the level of blood shown in the veins of the optic disc. Similarly, or alternatively, the haemoglobin level of the patient can be determined from the image of the macula.

Figure 3A:
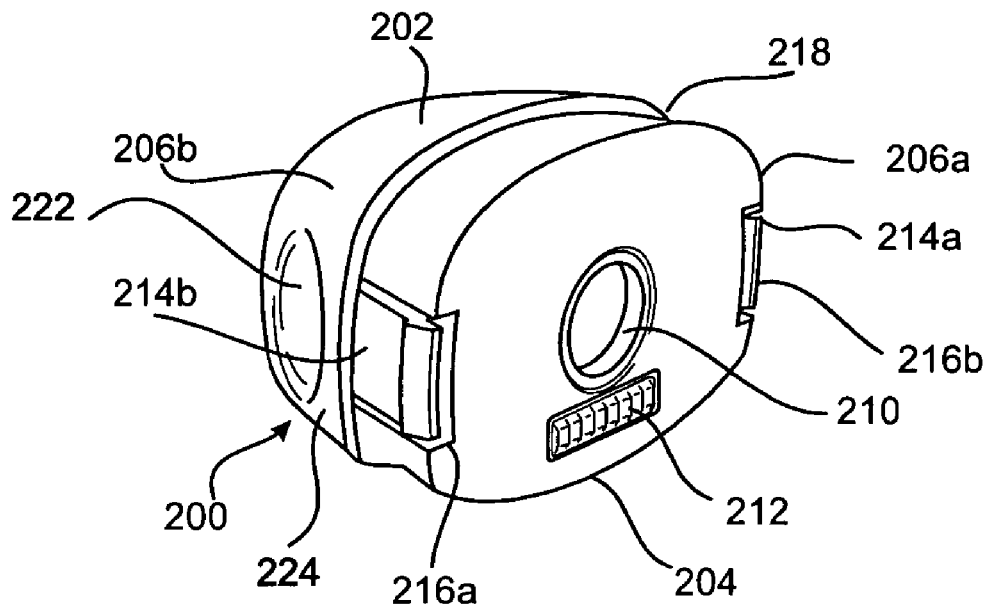
FIGS. 3a and 3b are isometric views of an ophthalmic camera adaptor of the present invention.
Figure 3B:
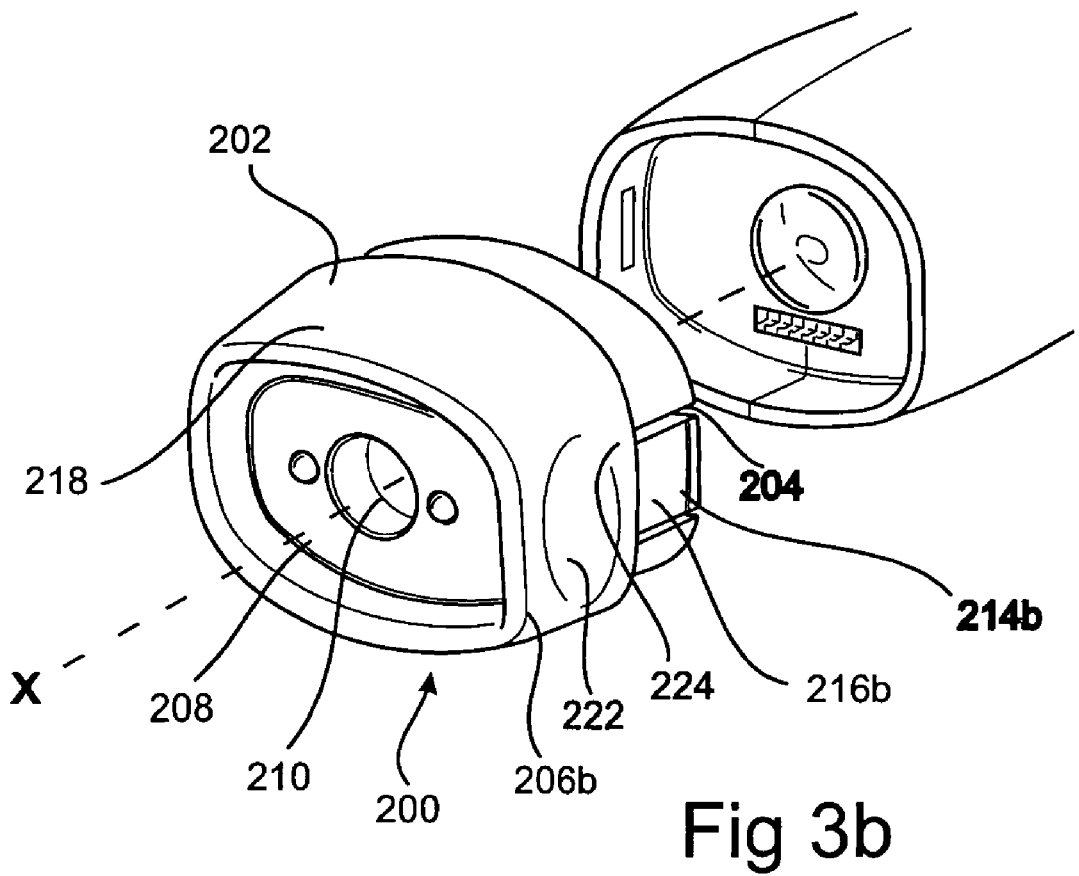
Figure 4:
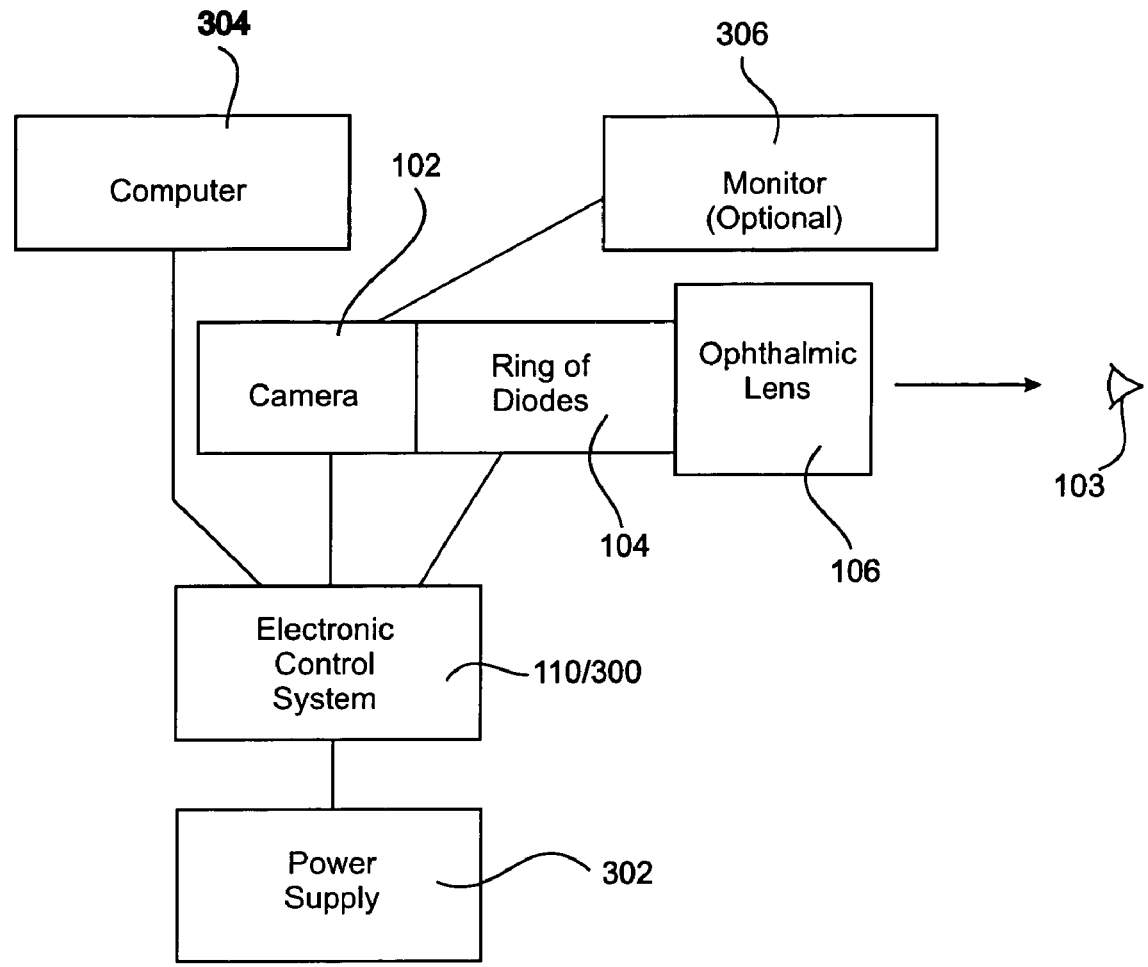
FIG. 4 is a block diagram of an embodiment of the ophthalmic camera of the present invention.
Figure 5:
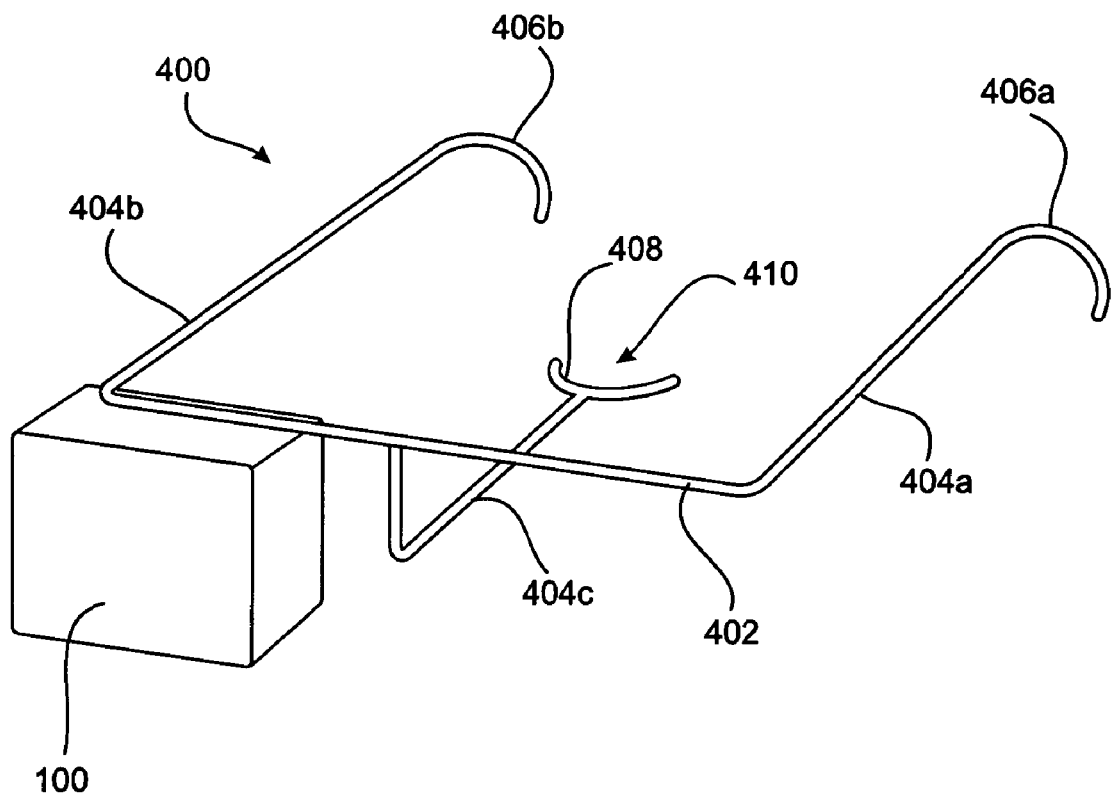
FIG. 5 is an isometric view of a frame arrangement for the ophthalmic camera of the present invention with the ophthalmic camera situate thereon.

In accordance with a second embodiment of the invention, where like numerals reference like parts, there is an ophthalmic camera adaptor 200. The ophthalmic camera adaptor 200 is shown in FIGS. 3a and 3b.

The ophthalmic camera adaptor 200 consists of a body 202. In the embodiment being described, body 202 is substantially rectangular in shape and has a rear face 204, two sides 206a, 206b and a front face 208.

Located centrally about rear face 204 is an aperture 210. Aperture 210 extends through the ophthalmic adaptor 200 such that aperture 210 is also located centrally about front face 208. Situate adjacent aperture 210 is an interface contact 212.

Adjacent face 204 are two snap clips 214a, 214b. Snap clip 214a extends from side 206a, while snap clip 214b extends from side 206b. Each snap clip 214 has an internal recess 216 positioned such that, when appropriate pressure is applied, the snap clips 214 can flex towards aperture 210. Snap clips 214a, 214b are adapted to be releasably retained within grooves on the body of a camera (not shown) to which it is ultimately attached.

Surrounding front face 208, and extending along a portion of sides 206 towards rear face 204, is a rubber overmoulding 218. Rubber overmoulding 218 covers a portion 220 of each snap clip 214. Finger grips 222 are formed within the external surface 224 of rubber overmoulding 218 at a position substantially adjacent portion 220.

The optics of the ophthalmic adaptor 200 comprise a plurality of coloured LEDs 104 substantially equidistantly disposed around the circumference of aperture 210. The LEDs 104 comprise a blue LED 112, green LED 114, yellow LED 116, red LED 118, infrared 120 and white LED 123. The wavelengths of each LED 112, 114, 116, 118, 120,123 is as set out in respect of the first embodiment of the invention.

Each LED 104 is connected to the interface contact 212 such that control of the LEDs is facilitated through the interface contact 212.

The light emitted by each LED 104 is directed towards the ophthalmic lens 108 as described in the first embodiment of the invention. The ophthalmic lens 108 is positioned in the aperture 210 such that the ophthalmic lens 108 is substantially flush with front face 208. However, the ophthalmic lens 108 is capable of linear movement along aperture 210 so as to allow for focusing of the image to be captured.

When the ophthalmic adaptor 200 is releasably retained within the grooves on the body of the camera, the following situation exists:
aperture 210 aligns with the optical axis X of the camera, such that at least a portion of the optical axis X is not obscured by the remainder of the adaptor (excluding ophthalmic lens 108);
interface contact 212 forms a connection with the camera such that the camera may perform the same functions as control unit 110; and
the external surface 224 of rubber overmoulding 218 may sit flush with the external surface of the camera.

In accordance with a third embodiment of the invention, where like numerals refer to like parts, the control unit 110 is replaced with an electronic control system 300. The electronic control system 300 includes a power supply 302. The power supply 302, through electronic control system 300, provides power to the monochromatic camera 102 and LEDs 104. In all other respects, the electronic control system is equivalent to the control unit 110. The electronic control system is, however, connected to a computer 304.

Additionally, the monochromatic camera 102 is a digital camera with two output ports. The first output port is connected to computer 304. The second output port is optionally, connected to a monitor 306.

During use of the ophthalmic camera 100, details of the settings of the ophthalmic camera 100 are communicated to the computer 304 by the electronic control system 300. As images are captured, the monochromatic camera 102 also provides a digitised version of the image to computer 304. Software stored on computer 304 allows the combination of digitised image and setting details to be manipulated in a manner as desired by the user.

For instance, a pseudo-colour picture can be formed for diagnostic use by combining images captured using three different wavelength images. Alternatively, a monochromatic reference image may be taken using a single wavelength. The image can then be manipulated to create a 3-band false colour image. The false colour image can then be colour-matched with a colour image taken with a fundus camera (not shown) and the resulting colour-matched image used for diagnostic purposes.

The monitor 306 receives constant information from the monochromatic camera 102 representing the image presently within its optical axis X. In this manner, the user can, by viewing the image on monitor 305, decided whether to capture the then current image or not.

In accordance with a fourth embodiment of the invention, where like numerals reference like parts, there is provided a frame 400 for the ophthalmic camera of the first embodiment comprising a cross-member 402 and a plurality of supporting members 404.

Cross-member 402 is attached to supporting member 404a at one end thereof and attached to supporting member 404b at the other end.

Supporting member 404a and 404b are substantially perpendicular to cross-member 402 and substantially parallel to each other. At the unattached end of each supporting member 404a, 404b, is a curved hook-like arrangement 406a, 406b.

Supporting member 404c is "L"-shaped and attached at a point substantially central to cross-member 402. Supporting member 404c protrudes in the same direction relative to cross-member 402 as curved hook-like arrangements 406a, 406b. The portion of supporting member 404c not attached to cross-member 402 extends towards the curved hook-like arrangements 406a, 406b.

A "C"-shaped portion 408 is attached to the open end of supporting member 404c, such that the open area 410 of the "C"-shaped portion 408 is unobstructed.

Attached to cross-member 402 is the ophthalmic camera 100 of the first embodiment of the invention. The ophthalmic camera 100 can be moved along the full length of cross-member 402. Again, this arrangement is possible due to the minimal size of the optical setup of the ophthalmic camera 100.

The end result is that the frame 400 is similar in structure to standard glass frames.

In use, the operator of the ophthalmic camera 100 places the frame 400 on their face such that hook-like arrangements 406a, 406b fit around the ear of the operator and the open area 410 fo teh "C"-shaped portion 408 cups the nose of the operator.

When placed on the face of the operator, the ophthalmic camera 100 is spaced therefrom by the length of the supporting members 406. The operator may then operate the ophthalmic camera 100 as mentioned above to capture an image of one of the patient's eyes. Once the image is captured, the ophthalmic camera 100 can then be moved along cross-member 102 to allow an image to be captured of the patient's other eye.

The frame 400 is then removed from the face of the operator and the hook-like arrangements 406a, 406b inverted. The operator may then replace the frame on their face to capture an image of the patient's other eye.

In accordance with a fifth embodiment of the invention, where like numerals reference like parts, there is provided a frame 500 for the ophthalmic camera of the first embodiment comprising a cross-member 502 and plurality of supporting members 504.

Cross-member 502 is attached to supporting member 504a at one end thereof and attached to supporting member 504b at the other end.

Supporting members 504a and 504b are substantially perpendicular to cross-member 502 and substantially parallel to each other. At the unattached end of each supporting member 504a, 504b is a curved hook-like arrangement 506a, 506b. The hook-like arrangements 506a, 506b are capable of inversion.

Supporting member 504c is "L"-shaped and attached at a point substantially central to cross-member 502. Supporting member 504c protrudes in the same direction relative to cross-member 502 as curved hook-like arrangements 506a, 506b. The portion of supporting member 404c not attached to cross-member 502 extends towards the curved hook-like arrangements 506a, 506b.

A "C"-shaped portion 508 is attached to the open end of supporting member 504c such that the open area 510 of the "C"-shaped portion 508 is unobstructed.

Attached to cross-member 502 at a position between supporting members 504c and 504a or between supporting members 504c and 504b is the ophthalmic camera 100 of the first embodiment of the invention. The ophthalmic camera 100 can be moved along the cross-member 502, the movement of the ophthalmic camera 100 being bound by supporting member 504a and 504c or supporting members 504c and 504b, as appropriate. This arrangement is possible due to the minimal size of the optical setup of the ophthalmic camera 100.

The end result is that the frame 500 is similar in structure to standard glass frames.

In use, the operator of the ophthalmic camera 100 places the frame 500 on their face such that hook-like arrangements 506a, 506b fit around the ear of the operator and the open area 510 of the "C"-shaped portion 508 cups the nose of the operator.

When placed on the face of the operator, the ophthalmic camera 100 is spaced therefrom by the length of the supporting members 506. The operator may then operate the ophthalmic camera 100 as mentioned above to capture an image of one of the patient's eyes.

The frame 500 is then removed from the face of the operator and the hook-like arrangements 506a, 506b inverted. The operator may then replace the frame on their face to capture an image of the patient's other eye.

It should be noted that the inversion means used in this embodiment must be semi-rigid to ensure that the frame 500 does not fall away from the operator's face through reason of an unintended inversion of the hook-like arrangements 506a, 506b.

In accordance with a sixth embodiment of the invention, where like numerals reference like parts, the fourth embodiment of the invention is modified to include a second ophthalmic camera 100. In this arrangement, the ophthalmic cameras 100 are identical in their configuration such that the operator can take pictures of both of the patient's eyes without the need for removal of the frame 400. It is therefore unnecessary, in this arrangement, for hook-like arrangements 406a, 406b to be invertible.

It should be appreciated by the person skilled in the art that the present invention is not limited to the above embodiments and that variations and modifications thereof are considered to be within the scope of the invention. In particular, the following modifications and variations fall within the scope of the invention:

monochromatic camera 102 may be replaced with a colour camera (which may or may not result in a need for other filters). Additionally, monochromatic camera 102, or colour camera (as appropriate), may be a digital camera or an analog camera coupled with digitising means for generating a digital representation of the analog image taken by the analog camera.

the ophthalmic lens 106 may be replaced with any other type of lens.

the ophthalmic camera 100 may include a spectrometer. In such an arrangement the image taken by the ophthalmic camera 100 may be analysed by the spectrometer to produce a spectroscopic graph of the image. The spectroscopic graph can then be used in measuring the glucose or haemoglobin levels of the patient. Alternatively, images taken by the ophthalmic camera 100 may be subjected to the afore-mentioned analysis by an external spectrometer.

the plurality of LEDs 104 may be set on a time delay arrangement, whereby each, or a subset of, LEDs 104 are illuminated in sequence and for a predetermined period of time;

the plurality of LEDs 104 may be replaced with a single LED disposed about the circumference of the camera lens 108;

the plurality of LEDs 104 may be arranged such that each LED 104 is of the same colour but of a differing wavelength.

the ophthalmic camera 100 and ophthalmic camera adaptor 100 may include magnification lenses. Each magnification lens is associated with at least one setting, such that, on choosing the setting, the magnification lens is positioned within the optical axis X of the monochromatic camera 102 and in-between the ophthalmic lens 116 and the camera lens 118.

An alternate number of settings may be used than has been described herein. Alternatively, rather than having settings that move the LEDs 104 to predefined positions, the linear and pivotal movement of LEDs 104 may be facilitated through separate manual controls.

The linear and pivotal movement of LEDs 104 may be facilitated through a single manual control.

Control unit 120 may be adapted to control the linear and pivotal movement of LEDs 104 based on the determined size of the pupil 121 to be examined.

the linear movement of the ophthalmic lens 108 as a means of focusing the image to be captured can be replaced by other focusing structures.

the adaptor structure mentioned above can be replaced with any other structure incorporating the optical arrangement mentioned.

the interface contract 212 may be omitted and in its place control unit 110 may be in-built into the adaptor.

image manipulation techniques or procedures, other than those mentioned above, may be used to create an image useful for diagnostic purposes.

power supply 302 may take the form of a mains adaptor or a battery.

the inversion means of frame 500 may take the form, amongst others, of deformable hook-like arrangements 506a, 506b or hook-like arrangements 506a, 506b that are rotatable about supporting members 506a, 506b respectively.

It should be further appreciated by the person skilled in the art that features and modifications discussed above, not being alternatives or substitutes, can be combined to form yet other embodiments that fall within the scope of the invention described.

We claim:

1. An ophthalmic camera comprising:
    a camera having a camera lens;
    at least one illumination means; and
    an ophthalmic lens,
        where, the centres of the ophthalmic lens and camera lens are aligned to form an alignment axis and where the at least one illumination means is capable of linear movement along a radial axis of the camera lens and pivotal movement about the radial plane incorporating radial axis and alignment axis, such that the circle of light emitted by the at least one illumination means is constantly directed to the centre of the ophthalmic lens.

2. The ophthalmic camera according to claim 1, further comprising selection means for choosing from a plurality of settings, each setting representing a pupil size or range of pupil sizes, such that, when the setting is changed, the at least one illumination means moves linearly along its radial axis to the position specified by the new setting and pivots about the radial plane until the circle of light emitted by the at least one illumination means is directed on the centre of the ophthalmic lens.

3. The ophthalmic camera according to claim 1, where the linear and pivotal movement of the at least one illumination means is controlled by one or more manual controls.

4. The ophthalmic camera according to claim 1, further comprising automated measuring means for obtaining a measurement of the size of the pupil to be examined, the automated measuring means also controlling the linear and pivotal movement of the at least one illumination means to a position determined best for the measured pupil size.

5. The ophthalmic camera according to claim 1, further comprising at least one magnification lens, each magnification lens being associated with at least one linear position of the at least one illumination means, such that the linear position of the at least one illumination means determines which magnification lens are positioned within the alignment axis.

6. The ophthalmic camera according to claim 1, where one of the at least one illumination means has a wavelength in the range 450 to 490 nm.

7. The ophthalmic camera according to claim 6, where the illumination means has a wavelength of 490 nm.

8. The ophthalmic camera according to claim 1, where one of the at least one illumination means has a wavelength in the range 491 to 559 nm.

9. The ophthalmic camera according to claim 8, where the illumination means has a wavelength of 540 nm.

10. The ophthalmic camera according to claim 1, where one of the at least one illumination means has a wavelength in the range 560 to 595 nm.

11. The ophthalmic camera according to claim 10, where the illumination means has a wavelength of 590 nm.

12. The ophthalmic camera according to claim 1, where one of the at least one illumination means has a wavelength in the range 596 to 699 nm.

13. The ophthalmic camera according to claim 12, where the illumination means has a wavelength of 630 nm.

14. The ophthalmic camera according to claim 1, where one of the at least one illumination means has a wavelength of 700 nm.

15. The ophthalmic camera according to claim 1, where one of the at least one illumination means produces white light.

16. The ophthalmic camera according to claim 1, the camera is a digital camera or an analogue camera with digitising means for producing a digital representation of analogue images taken by the analogue camera.

17. The ophthalmic camera according to claim 1, where the at least one illumination means, or a subset of the at least one illumination means, is illuminated in accordance with a predetermined sequence.

18. The ophthalmic camera according to claim 1 including at least one interface means for connecting to at least one of the following: an external computer, an external monitor, an external spectrometer.

19. The ophthalmic camera according to claim 1, further comprising a spectrometer, the spectrometer operable to produce a spectroscopic graph of images taken by the camera.

20. The ophthalmic camera according to claim 1, where the at least one illumination means is of variable intensity.

21. The ophthalmic camera according to claim 20, where the level of intensity of the at least one illumination means is a function of a pupil colour setting of the ophthalmic camera.

22. The ophthalmic camera according to claim 1, where each of the at least one illumination means surrounds the circumference of the camera lens.

23. The ophthalmic camera according to claim 22, where each illumination means is equidistant from its adjacent illumination means.

24. The ophthalmic camera according to claim 1, where the illumination means are solid state light emitting diodes.

25. The ophthalmic camera according to claim 1, where the illumination means comprises light bulbs and a light focusing means.

26. The ophthalmic camera according to claim 1, where the camera has a high sensitivity to low light.

27. The ophthalmic camera according to claim 26, where the sensitivity level of the camera is <0.05 lux.

28. The ophthalmic camera according to claim 1, where the camera lens is between 5 and 8 mm in diameter.

29. The ophthalmic camera according to claim 1, where the ophthalmic lens is in the range of 20 to 40 dioptres.

30. The ophthalmic camera according to claim 29, where the ophthalmic lens is 20 dioptres.

31. The ophthalmic camera according to claim 1, further comprising focusing means.

32. The ophthalmic camera according to claim 31, where the focusing means takes the form of movement means operable to move the ophthalmic lens linearly along the alignment axis.

33. The ophthalmic camera according to claim 1, where the ophthalmic lens is equal to or smaller than the camera lens in size.

34. An ophthalmic camera adaptor comprising:
at least one illumination means; and
an ophthalmic lens,
where, the centres of the ophthalmic lens and camera lens are aligned to form an alignment axis and where the at least one illumination means is capable of linear movement along a radial axis of the camera lens and pivotal movement about the radial plane incorporating radial axis and alignment axis, such that the circle of light emitted by the at least one illumination means is constantly directed to the centre of the ophthalmic lens.

35. The ophthalmic camera adaptor according to claim 34, further comprising selection means for choosing from a plurality of settings, each setting representing a pupil size or range of pupil sizes, such that, when the setting is changed, the at least one illumination means moves linearly along its radial axis to the position specified by the new setting and pivots about the radial plane until the circle of light emitted by the at least one illumination means is directed on the centre of the ophthalmic lens.

36. The ophthalmic camera adaptor according to claim 34, where the linear and pivotal movement of the at least one illumination means is controlled by one or more manual controls.

37. The ophthalmic camera adaptor according to claim 34, further comprising automated measuring means for obtaining a measurement of the size of the pupil to be examined, the automated measuring means also controlling the linear and pivotal movement of the at least one illumination means to a position determined best for the measured pupil size.

38. The ophthalmic camera adaptor according to claim 34, further comprising at least one magnification lens, each magnification lens being associated with at least one linear position of the at least-one illumination means, such that the linear position of the at least one illumination means determines which magnification lens are positioned within the alignment axis.

39. The ophthalmic camera adaptor according to claims 34, where one of the at least one illumination means has a wavelength in the range 450 to 490 nm.

40. The ophthalmic camera adaptor according to claim 39, where the illumination means has a wavelength of 490 nm.

41. The ophthalmic camera adaptor according to claim 34, where one of the at least one illumination means has a wavelength in the range 491 to 559 nm.

42. The ophthalmic camera adaptor according to claim 41, where the illumination means has a wavelength of 540 nm.

43. The ophthalmic camera adaptor according to claim 34, where one of the at least one illumination means has a wavelength in the range 560 to 595 nm.

44. The ophthalmic camera adaptor according to claim 43, where the illumination means has a wavelength of 590 nm.

45. The ophthalmic camera adaptor according to claim 34, where one of the at least one illumination means has a wavelength in the range 596 to 699 nm.

46. The ophthalmic camera adaptor according to claim 45, where the illumination means has a wavelength of 630 nm.

47. The ophthalmic camera adaptor according to claim 34, where one of the at least one illumination means has a wavelength of 700 nm.

48. The ophthalmic camera adaptor according to claim 34, where one of the at least one illumination means produces white light.

49. The ophthalmic camera adaptor according to claim 34, where the at least one illumination means, or a subset of the at least one illumination means, is illuminated in accordance with a predetermined sequence.

50. The ophthalmic camera adaptor according to claim 34, where the at least one illumination means is of variable intensity.

51. The ophthalmic camera adaptor according to claim 50, where the level of intensity of the at least one illumination means is a function of a pupil colour setting of the ophthalmic camera adaptor.

52. The ophthalmic camera adaptor according to claim 34, where the illumination means are solid state light emitting diodes.

53. The ophthalmic camera adaptor according claim 34, where the illumination means comprises light bulbs and a light focusing means.

54. The ophthalmic camera adaptor according to claim 34, where the ophthalmic lens is in the range of 20 to 40 dioptres.

55. The ophthalmic camera adaptor according to claim 54, where the ophthalmic lens is 20 dioptres.

56. The ophthalmic camera adaptor according to claim 34, further comprising focusing means.

57. The ophthalmic camera adaptor according to claim 56, where the focusing means takes the form of movement means operable to move the ophthalmic lens linearly along the alignment axis.

58. The ophthalmic camera adaptor according to claim 34, where the ophthalmic lens is equal to or smaller in size to the lens of the camera to which the ophthalmic camera adaptor attaches.

59. A wearable frame having at least one ophthalmic camera according to claim 1 fixed thereon.

60. A wearable frame having at least one ophthalmic camera according to claim 1 slidably mounted thereon.

61. A method of determining a glucose level of a patient using the camera of claim 1, comprising:
- emitting a beam of light having a wavelength in the range 570 to 590nm into a pupil of the patient;
- taking an image of the pupil using the camera of claim 1 which has an associated ophthalmic lens of at least 20x magnification; and
- determining the glucose level of the patient from the level of blood in the veins of the optic disc.

62. A method of determining a haemoglobin level of a patient using the camera of claim 1, comprising:
- emitting a beam of light having a wavelength in the range 570 to 590nm into a pupil of the patient;
- taking an image of the pupil using the camera of claim 1 which has an associated ophthalmic lens of at least 20x magnification; determining the haemoglobin level of the patient from the image of the macula.

63. A method of determining a glucose level of a patient using the ophthalmic camera adaptor of claim 34, comprising:
- emitting a beam of light having a wavelength in the range 570 to 590nm into a pupil of the patient;
- taking an image of the pupil using a camera and the ophthalmic camera adaptor of claim 34 which has an associated ophthalmic lens of at least 20x magnification; and
- determining the glucose level of the patient from the level of blood in the veins of the optic disc.

64. A method of determining a haemoglobin level of a patient using the ophthalmic camera adaptor of claim 34, comprising:
- emitting a beam of light having a wavelength in the range 570 to 590nm into a pupil of the patient;
- taking an image of the pupil using a camera and the ophthalmic camera adaptor of claim 34 which has an associated ophthalmic lens of at least 20x magnification;
- determining the haemoglobin level of the patient from the image of the macula.

* * * * *